United States Patent [19]
Chen et al.

[11] Patent Number: 5,120,900
[45] Date of Patent: Jun. 9, 1992

[54] INTEGRATED SOLVENT EXTRACTION/MEMBRANE EXTRACTION WITH RETENTATE RECYCLE FOR IMPROVED RAFFINATE YIELD

[75] Inventors: Tan-Jen Chen, Clearwater, Canada; James R. Sweet, Baton Rouge, La.

[73] Assignee: Exxon Research and Engineering Company, Florham Park, N.J.

[21] Appl. No.: 624,807

[22] Filed: Dec. 5, 1990

[51] Int. Cl.[5] .................... C07C 7/00; C07C 7/144; B01D 61/00

[52] U.S. Cl. .................................... 585/804; 585/818; 585/819; 585/857; 585/863; 585/864; 210/644; 210/650; 210/651; 208/308; 208/327; 208/330; 208/335

[58] Field of Search ............... 585/818, 819, 804, 857, 585/863, 864; 210/644, 650, 651; 208/308, 327, 330, 335

[56] References Cited

U.S. PATENT DOCUMENTS

| | | | |
|---|---|---|---|
| 2,930,754 | 3/1960 | Stuckey | 210/23 |
| 2,947,687 | 8/1960 | Lee | 585/818 |
| 2,958,656 | 11/1960 | Stuckey | 210/23 |
| 3,244,763 | 4/1966 | Cahn | 260/677 |
| 3,370,102 | 2/1968 | Carpenter et al. | 260/674 |
| 3,476,681 | 11/1969 | Davies et al. | 208/326 |
| 3,843,515 | 10/1974 | MacDonald et al. | 208/326 |
| 3,956,112 | 5/1976 | Lee et al. | 210/22 |
| 4,057,491 | 11/1977 | Bushnell et al. | 208/321 |
| 4,115,465 | 9/1978 | Elfert et al. | 260/674 |
| 4,125,458 | 11/1978 | Bushnell et al. | 208/309 |
| 4,168,226 | 9/1979 | White et al. | 208/321 |
| 4,311,583 | 1/1982 | Woodle | 208/312 |
| 4,328,092 | 5/1982 | Sequeira, Jr. | 208/326 |
| 4,510,047 | 4/1985 | Thompson | 208/321 |
| 4,532,347 | 7/1985 | Vaughan | 562/528 |
| 4,592,832 | 6/1986 | Bristow et al. | 208/309 |
| 4,670,151 | 6/1987 | Bitter et al. | 210/641 |
| 4,828,773 | 5/1989 | Feimer et al. | 264/45.5 |
| 4,837,054 | 6/1989 | Schucker | 427/244 |
| 4,861,628 | 8/1989 | Schucker | 427/245 |
| 4,879,044 | 11/1989 | Feimer et al. | 210/654 |
| 4,914,064 | 4/1990 | Schucker | 502/4 |
| 4,929,357 | 5/1990 | Schucker | 210/640 |
| 4,929,358 | 5/1990 | Koenitzer | 210/640 |
| 4,962,271 | 10/1990 | Black et al. | 585/819 |
| 4,966,707 | 10/1990 | Cussler et al. | 210/632 |

FOREIGN PATENT DOCUMENTS 2595370  5/1988  France.
2595371  5/1988  France.

OTHER PUBLICATIONS

"Liquid Extraction" 2d Ed. R. E. Treybol, McGraw-Hill Book Co. 1963 pp. 144-145: 270-273.
"Microporous Membrane Solvent Extraction", Prasad, R., et al., Separation Science & Technology 22(2&3) 619-640, 1987.
"Dispersion-Free Solvent Extraction with Microporous Hollow Fiber Modules" Prasad, R., et al. AIChE Summer National Meeting Boston, 1986.
"Designing Hollow Fiber Contactors" Yang, M. C., et al. AIChE Journal Nov. 1986, vol. 32, No. 11, pp. 1910-1916.
"Liquid-Liquid Extractions with Microporous Hollow Fibers" D'Elia, N. A., et al. J. Memb. Sci. 29 (1986) 309-319.
"Critical Entry Pressure For Liquids in Hydrophobic Membranes", Kim, B. S., et al. J. Coll. & Interface Sci., vol. 115, No. 1, 1987, pp. 1-8.

(List continued on next page.)

Primary Examiner—Anthony McFarlane
Assistant Examiner—Nhat Phan
Attorney, Agent, or Firm—Joseph J. Allocca

[57] ABSTRACT

Raffinate yield from solvent extraction is improved when the extract phase recovered from the solvent extraction process is subjected to a membrane separation step wherein a saturates/1-ring aromatics rich retentate is produced and a 2+ ring aromatics rich permeate are produced and the saturates/1-ring aromatic rich retentate phase is recycled to the solvent extraction process.

8 Claims, 2 Drawing Sheets

OTHER PUBLICATIONS

"Solvent Extraction with Microporous Hydrophilic and Composite Membranes", Prasad, R., et al. AIChE Journal, vol. 33, No. 7, 1987 (pp. 1057-1066).

"Dispersion-Free Solvent Extraction with Microporous Hollow Fiber Modules" Prasad, R., et al AIChE Journal, vol. 34, No. 2, (1988) pp. 177-187.

"Nondispersive Solvent Extraction Using Microporous Membranes", Prasad, R., et al. AIChE Symposium Series, Membrane Materials & Proc., No. 261, vol. 84, 1988 pp. 42-53.

"Hollow Fiber Solvent Extraction of Pharmaceutical Products: A Case Study" Prasad, R., et al. J. Memb. Sci. 47 (1989) pp. 235-259.

"Novel Uses of Microporous Membranes: A Case Study" R. W. Callahan, AIChE Symposium Series, Membrane Materials & Proc., No. 261, vol. 84, 1988, pp. 54-65.

INTEGRATED SOLVENT EXTRACTION/MEMBRANE EXTRACTION WITH RETENTATE RECYCLE FOR IMPROVED RAFFINATE YIELD

BACKGROUND OF THE INVENTION FIELD OF THE INVENTION

The present invention is a method whereby yield of saturates/1-ring aromatics rich raffinate obtained by the solvent extraction of a hydrocarbon feed is increased by a process involving the steps of solvent extracting a hydrocarbon feed to produce a raffinate phase and an extract phase, removing the extraction solvent from the extract phase by, for example, distillation to produce an extract oil passing the extract oil to a membrane separation process wherein a saturates/1-ring aromatics rich retentate is produced as is a 2+ ring aromatics rich permeate phase and recycling the saturates/1-ring aromatics rich retentate back to the solvent extraction process for addition to the hydrocarbon feed for processing in the solvent extraction process.

The amount of saturates/1-ring aromatics rich raffinate obtained by this integrated process is greatly enhanced as compared to the yield obtained without the recycle of the membrane produced retentate phase to the solvent extraction zone.

DESCRIPTION OF THE RELATED ART

Removal of aromatic hydrocarbons from hydrocarbon feed streams such as fuels or lubes or specialty products (e.g. refrigerator, turbine, electrical insulating or white oils) is a commonly practiced process. This is so because the presence of aromatics in such hydrocarbon products is usually detrimental to their performance and commercial unacceptability.

Aromatic hydrocarbons in lube oil fractions have been associated with reduced viscosity indexes and poor stability to oxidation and light. For this reason it is generally beneficial to remove the aromatics.

Despite this generally accurate statement, however, it is equally true that not all aromatics are undesirable lube components or detrimental to performance or quality.

Poor oxidation and light stability is now associated with the polynuclear aromatic compounds, i.e. the multi-ring aromatics. Indeed, the presence of 1-ring aromatics in a lube oil fraction may be beneficial with regards to viscosity index and oxidation and light stability. One-ring aromatics which are heavily branched with alkyl side chains are now viewed as being desirable lube oil constituents.

The typical way to remove aromatic hydrocarbons from hydrocarbon feeds is by solvent extraction. In such a process the hydrocarbon feed is introduced into an extraction zone and contacted with a selective aromatic extraction solvent moving counter currently. Typical aromatics extraction solvents include phenol, furfural, sulfolane, and N-methyl 2-pyrrolidone (NMP).

The use of the preferred solvent NMP (with or without minor amounts of water present) to selectively extract aromatic constituents from oil streams is the subject of many patents including U.S. Pat. No. 3,843,515, U.S. Pat. No. 3,476,681, and U.S. Pat. No. 4,125,458 hereby incorporated by reference. U.S. Pat. No. 4,057,491 and U.S. Pat. No. 4,168,226 (hereby incorporated by reference) are fairly representative of typical NMP recovery processes and demonstrate the large energy requirements encountered.

The solvent extraction process produces a raffinate rich in saturates and an extract lean in saturates and rich in aromatics present in the extraction solvent.

The raffinate is recovered for use as a lubes base stock while the extract, following solvent recovery to yield an extract oil, is used as cat cracker feed, burnt as fuel or sent to a coker.

Despite this use, however, the solvent free extract oil contains valuable lube molecules which are lost.

It would be an advantage if the valuable lube molecules in the extract oil could be recovered.

SUMMARY OF THE INVENTION

The yield of raffinate obtained from a solvent extraction process practiced on a hydrocarbon feed is increased by a process involving the steps of solvent extracting the hydrocarbon feed to produce a raffinate phase and an extract phase, removing solvent from the extract phase to produce an extract oil, passing the extract oil to a membrane separation process wherein a saturates/1-ring aromatics rich retentate is produced as is a 2+ ring aromatics rich permeate and recycling the retentate to the solvent extraction process for addition to the hydrocarbon feed for processing in the solvent extraction process.

DESCRIPTION OF THE PREFERRED EMBODIMENTS

Figure 1:
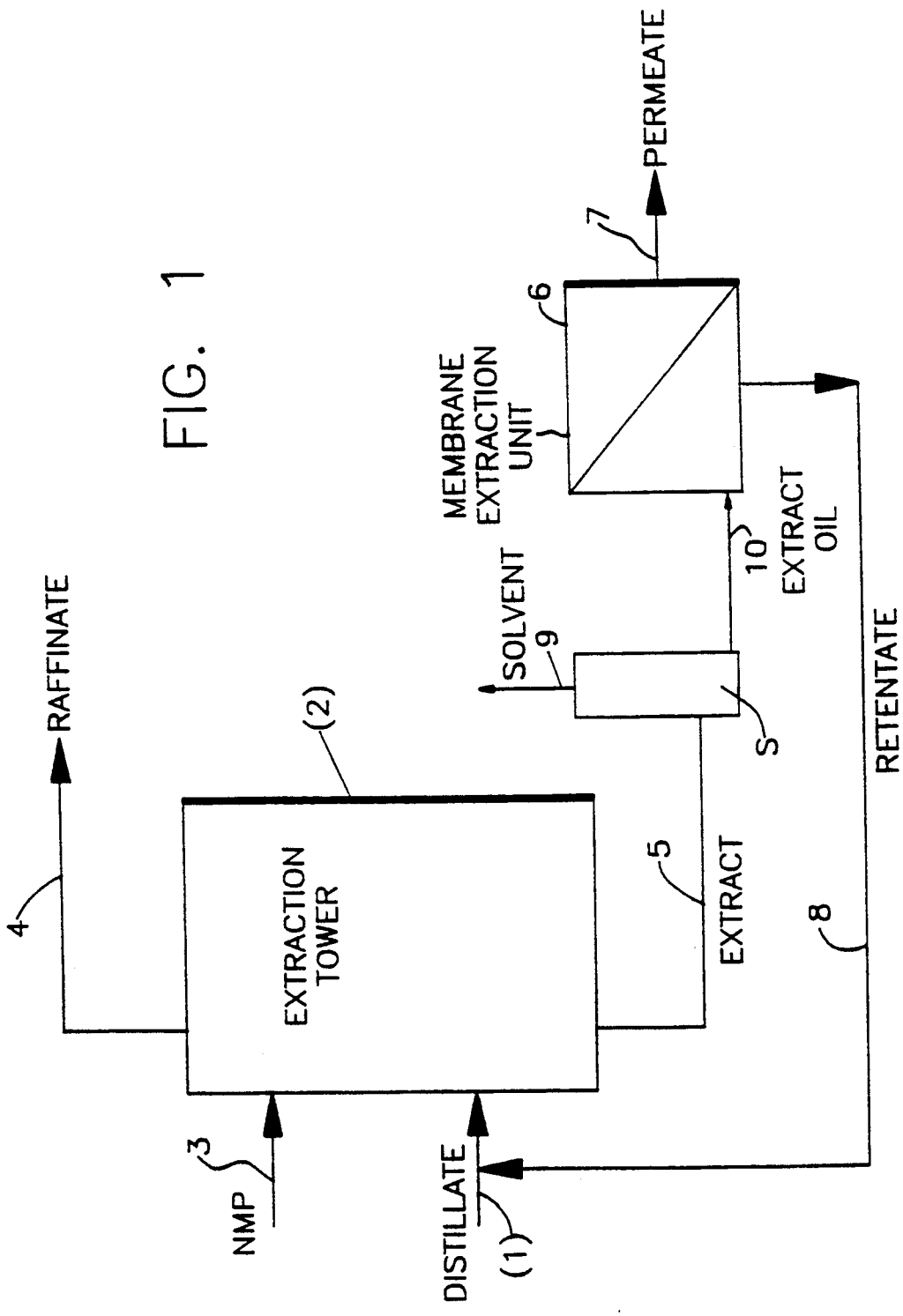
FIG. 1 is a schematic of the integrated process of the present invention showing retentate phase recycle to produce enhanced yield of raffinate.

The yield of valuable raffinate material recovered from a conventional solvent extraction process can be increased by a process comprising the steps of integrating the solvent extraction process with a membrane separation process which uses the solvent free extract oil as feed to the membrane unit to produce a saturates/1-ring aromatics rich retentate phase for recycling to the solvent extraction zone. The retentate is recycled to the solvent extraction zone in an amount ranging from 5 to 50 wt. %, preferably 20 to 33 wt. % based on feed, expressed differently, the feed to retentate ratio ranges from 20 to 1 to 1 to 1, preferably 5/1 to 3/1.

The process, therefore, comprises the steps of passing an aromatics containing hydrocarbon feed to a solvent extraction zone, contacting the feed with an aromatics selective extraction solvent to produce a saturate rich raffinate and an aromatics rich extract, removing the solvent from the extract phase by, for example, distillation to recover an extract oil passing the extract oil to a membrane separation zone wherein the saturates and 1-ring aromatics are concentrated in a retentate phase and the 2+ ring aromatics are concentrated as a permeate phase and recycling the retentate phase to the solvent extraction zone for combining with the hydrocarbon feed in said zone and subjecting the combined feed to solvent extraction producing a raffinate phase of increased yield.

The process of the present invention may be practiced on any aromatics containing hydrocarbon feed stream from which it is desired to remove the aromatics and produce a saturate rich raffinate. The hydrocarbon stream can be any light to heavy material coming from any source, natural petroleum or synthetic stream such as coal liquefaction products, tar sands, or shale oil products. The hydrocarbon feed will be any light to heavy fraction, usually a distillate fraction boiling in the about 320° to about 1100° F. range. This embraces the jet and kerosene fraction (320°-500° F.) through diesel (400°-650° F.) into lube (600° to 1100° F.) including Bright Stock.

Selective aromatics extraction solvents which may be used in the solvent extraction process include any of the well known materials such as phenol, furfural, sulfolane, and n-methyl-2-pyrrolidone (NMP).

Following solvent recovery the extract oil from the solvent extraction process is sent as feed to a membrane separation zone wherein a retentate rich in saturates and 1-ring aromatics is produced and a permeate rich in 2+ ring aromatics is produced.

The membrane separation zone can include the system described in U.S. Pat. No. 3,370,102 which separates aromatics from saturates in a wide variety of feed mixtures including various petroleum fractions, naphthas, oils, and other hydrocarbon mixtures. Expressly recited in '102 is the separation of aromatics from kerosene. The process produces a permeate stream and a retentate stream and employs a sweep liquid to remove the permeate from the face of the membrane to thereby maintain the concentration gradient driving force. U.S. Pat. No. 2,958,656 teaches the separation of hydrocarbons by type i.e. aromatics, unsaturated, saturated by permeating a portion of the mixture through a non-porous cellulose ether membrane and removing permeate from the permeate side of the membrane using a sweep gas or liquid. U.S. Pat. No. 2,930,754 teaches a method for separating hydrocarbons by type, i.e. aromatics and/or olefins from gasoline boiling range mixtures by the selective permeation of the aromatics through certain cellulose ester non-porous membranes. The permeated hydrocarbons are continuously removed from the permeate zone using a sweep gas or liquid. U.S. Pat. No. 4,115,465 teaches the use of polyurethane membranes to selectively separate aromatics from saturates via pervaporation.

U.S. Pat. No. 4,914,064 teaches polyurea/-urethane membranes and their use for the separation of aromatics from non-aromatic hydrocarbon. The membrane is characterized by possessing a urea index of at least 20% but less than 100%, an aromatic carbon content of at least 15 mole %, a functional group density of at least about 10 per 1000 grams of polymer and a C=O/NH ratio of less than about 8.

Thin film composites can be prepared either from suspension deposition as taught in U.S. Pat. No. 4,861,628 or from solution deposition as taught in U.S. Pat. No. 4,837,054.

In U.S. Pat. No. 4,861,628, the thin film composite membrane constituting a thin layer of polymer deposited on a thick-permeable support layer is produced by preparing a fine dispersion of discrete polyurea/urethane polymer particles in a solvent which does not react with or dissolve the selected thick-permeable support layer. The dispersion is contacted with only one face of the support layer. The solvent is permitted to evaporate and the composite membrane results. The support layer will generally have pores ranging from 0.005 to 0.5 microns. Typical support include polyamide, polyimide, polyacrylonitrile, polybenzimidazole, teflon, cellulose acetate and polyolefins such a polyethylene and polypropylene.

Thin film composites can also be produced from solutions, as taught in U.S. Pat. No. 4,837,054. In that procedure the polyurea/urethane copolymer is prepared in a solution consisting of (a) an aprotic solvent such as dimethylformamide (DMF) (b) a cyclic ether such as dioxane, (c) cellosolve acetate or methyl cellosolve and (d) a wetting agent such as crotyl alcohol to produce a casting solution which is then deposited as a thin film onto a microporous support, excess solution permitted to drain from the support, and the solvent permitted to evaporate leaving a thin active layer on the support backing. Supports which are insoluble in the solvents used to produce the casting solution are e.g. polyolefin (e.g. polyethylene and polypropylene) and teflon. The support possess a molecular weight cut-off in the range of about 10,000 to 100,000. The solvent is used in a parts per hundred ratio of a/b/c/d in the range about 3-27/94-33/2-33/1-7. The polymer concentration in the solution can range up to about 40 parts or more polymer in the solution based on 100 parts solvent. Preferred polymer concentration is in the range 0.5 to 20 parts polymer, preferably 1-10 parts polymer, more preferably 1-5 parts polymer per 100 parts solvent.

The solvent is permitted to evaporate with the application of heat if needed to drive off the solvent. If a solvent of a low enough vapor pressure is employed the application of heat can be omitted.

The preparation of an anisotropic polyurea/-urethane membrane is the subject of U.S. Pat. No. 4,828,773 and U.S. Pat. No. 4,879,044. The preferred anisotropic membrane is produced by preparing a casting solution of the polyurea/urethane copolymer having the above recited characteristics in a solvent containing less than about 5 vol. % non-solvent, preferably about 0 vol. % non-solvent, the preferred solvent being dimethylformamide, to produce a casting solution. A thin film of the casting solution is deposited on a support having a maximum pore size of less than about 20 microns (e.g. glass, metal, release paper, etc.), exposing the thin film on support to conditions of temperature and time such that the solvent vapor pressure-time factor is about 1000 mm Hg-min and less, preferably about 200 mm Hg-min and less, and quenching the membrane film in a non-solvent such as water yielding the desired anisotropic membrane. The anisotropic membrane produced possesses a three layer structure, a thin dense layer generated at the film/support interface, a thin non-continuous skin which is generated at the membrane-quench solvent interface and an open, porous structure which exists between the aforementioned thin dense layer and thin non-continuous skin layer.

Polyurethane imides are produced by endcapping a polyol selected from those recited above with a polyisocyanate also selected from those recited above followed by chain extending by reaction with a polyanhydride which produces the imide directly or with di or poly carboxylic acids which produce amic acid groups which can be chemically or thermally condensed/cyclized to the imide. Aliphatic and cycloaliphatic di- and polyisocyanates can be used as can be mixtures of aliphatic, cycloaliphatic, aralkyl and aromatic polyisocyanates. Polyurethane imide membranes and their use for aromatics/non-aromatics separation are the subject of U.S. Pat. No. 4,929,358.

Isocyanurate crosslinked polyurethane membranes and their use for the separation of aromatics from non-aromatics is the subject of U.S. Pat. No. 4,929,357. The isocyanurate crosslinked polyurethane membrane is produced by preparing an end capped isocyanate pre-polymer of polyurethane by reacting dihydroxy or polyhydroxy compounds (e.g. polyethers or polyesters) with aliphatic, alkylaromatic or aromatic di or poly isocyanates and trimerizing this isocyanate end-capped polyurethane using a standard trimerization catalyst such as N,N',N"-tris(dimethylaminopropyl)-s-hexahydrotriazine, Sodium ethoxide, Potassium octoate, N-Hydroxypropyl-trimethylammonium-2-ethylhexanote, Potassium 2-ethylhexanoate, Trialkylphosphines, 2,4,6-Tris(dimethylaminomethyl)phenol and mixtures thereof. Using these catalyst yields a mixture which slowly thickens due to crosslinking accounted for by the formation of isocyanurate crosslinked rings. Before this mixture becomes too thick, it is deposited as a thin film on an appropriate substrate and permitted to fully gel, after which the membrane coat is treated to complete the formation of isocyanurate crosslinked polyurethane. This final treat can constitute no more than waiting a sufficiently long time to be certain that trimerization is complete. More likely this final treat will involve various degrees of drying followed, preferably, by heating to complete the trimerization to the isocyanurate crosslinked polyurethane.

U.S. Ser. No. 452,887, filed Dec. 19, 1989 in the names of Black and Shucker, now U.S. Pat. No. 4,962,271 teaches the selective separation of multi-ring aromatic hydrocarbons from distillates by perstraction. The multi-ring aromatics are characterized by having less than 75 mole % aromatic carbon content. Perstractive separation is through any selective membrane, preferably the aforesaid polyurea/urethane, polyurethane imides or polyurethane isocyanurates.

The previously described membranes and processes are all useful for separating aromatics from non-aromatics/saturates mixtures from a variety of feeds. It is herein envisioned that such membranes and processes can be practiced on a selective extraction extract oil to produce a multi-ring aromatics enrich permeate and a saturates rich retentate and that, in accordance with the teaching of the present specification, the retentate can be recycled to the solvent extraction zone for further extraction in combination with fresh feed to produce an enhance raffinate yield.

A preferred membrane separation procedure, however, is the subject of copending application U.S. Ser. No. 07/622,706, now U.S. Pat. No. 5,045,206 in the names of Chen and Sweet. In that specification it is taught that multi-ring aromatics, i.e. 2+ ring aromatics containing alkyl and heteroatom alkyl side chains and even heteroatom containing multi-ring aromatics such as benzo thiophene and dibenzo thiophene and quinoline can be selectively separated from a hydrocarbon feed such as distillate or even a solvent extraction extract oil using a procedure involving passing the hydrocarbon feed along one face of a non-selective, porous, partition barrier membrane while simultaneous passing, preferably in countercurrent flow, along the opposite side of said membrane a selective extraction solvent such as phenol, furfural, acetonitrile sulfolane, N-methyl 2-pyrrolidone, an aliphatic polyamine such as ethylene diamine, diethylene triamine or triethylene tetramine, dimethylsulfoxide (DMSO) etc. and mixtures thereof. The multi-ring aromatic selectively permeates through the membrane in response to the selective extraction solvent yielding a retentate rich in saturates and 1-ring aromatics and a permeate rich in multi-ring aromatics.

The alkyl substituted and alkyl/heteroatom substituted multi-ring aromatics and heteroatom containing multi ring aromatics have less than 75 mole % aromatic carbon. The multi-ring aromatics have at least 2, preferably 3 or more rings, preferably fused rings and one or more alkyl side chains of about 6 to 12 carbon atoms or more in length. The term multi-ring aromatics is used in this specification and the appended claims is meant to include condensed and fused ring aromatics as well as molecules such as biphenyl, diphenyl methane, tri phenyl methane, quinoline, carbozol, phenyl thiophene, benzo-thiophene, dibenzo thiophene etc. and spiro system aromatics consisting of two rings sharing a common atom.

The process makes use of a highly porous partition barrier. The barrier may be an ultrafiltration membrane made of ceramic, sintered glass or metal or of a polymeric material such as polyethylene, polypropylene, teflon, cellulose, nylon, etc. and generally has a pore size in the range 100 to 5000 Å. The membrane is, preferably, hydrophobic in nature.

The extract oil feed and extraction solvent can be contacted at any temperature so long as both the feed and solvent are in the liquid state. Because the separation process is driven by the affinity of the extraction solvent for the aromatic molecules, the process can be run at atmospheric pressure. Indeed, because of the high porosity of the membrane partition barrier the existence of a pressure differential, either by the direct application of pressure on the feed or solvent side or the creation of a vacuum on either side is undesirable as such a pressure differential would physically force feed or solvent across the barrier and thus defeat its purpose.

The multi-ring aromatics rich permeate phase in the extraction solvent may be separated from said solvent by any known technique such as distillation or selective permeation of the solvent through a membrane. The selective separation of extraction solvents from aromatic extracts is the subject of U.S. Pat. No. 4,510,047 which shows such selective solvent permeation through a regenerated cellulose membrane and U.S. Ser. No. 417,333 which teaches the recovery of extraction solvent using interfacially polymerized membranes.

In the present process the retentate, which is a saturates/1-ring aromatics rich phase is recycled in an amount ranging from 5 to 50 wt. % based on feed, (i.e. a feed/retentate rate of 20/1 to 1/1) a feed/-retentate rate of preferably 20 to 33 wt. % based on feed, preferably 5/1 to 3/1 to the solvent extraction zone wherein, in combination with fresh feed, it is re-extracted. By this process the yield of raffinate is increased. The extract from the zone is subjected to membrane separation and the retentate is recycled, thus giving rise to an integrated continuous process.

The present invention is illustrated in FIG. 1. Fresh distillate feed is introduced via line (1) into the solvent extraction zone (2). Selective extraction solvent, in this case NMP is introduced via line (3) into zone (2) and countercurrently contacts the feed. A saturates rich raffinate phase is recovered via line (4). The aromatics rich extract phase is sent in line (5) to solvent recovery in separator (5) to yield recovered solvent in line (9) and an extract oil in line (10). The extract oil is recovered via line (10) and sent to a membrane separation unit (6)

wherein a multi ring aromatics rich permeate is produced and recovered via line 7. The saturates/1-ring aromatics rich retentate phase is recovered via line 8 and recycled to the extraction zone in an amount ranging from 5 to 50 wt. %, preferably 20 to 33 wt. % based on fresh feed, expressed differently, the fresh feed to recycle retentate ratio of the hydrocarbon fed to the extraction zone following start up, ranges from 20/1 to 1/1, preferably 5/1 to 3/1. The ratio employed in practice, is controlled to a major degree by the amount of extract solution recovered from the extraction tower and the amount of retentate produced in the membrane unit, and these are controlled by the nature of the fresh distillate feed sent to the extraction tower.

EXAMPLE

To illustrate the benefits of this integrated process, an extract oil sample (100N) was procured and subjected to membrane extraction; the retentate produced from membrane extraction was then solvent extracted in an admixture with a distillate feed. More specifically, in this study, in the membrane separation step, membrane extraction as described in copending application Ser. No. 07/622,706 filed in the names of Chen and Sweet even date herewith, now U.S. Pat. No. 5,045,206; was practiced to segregate the saturates and 1-ring aromatics from the 2+ ring aromatics in the extract, although perstraction or any other aromatics selective process could also be used to achieve the desired aromatics/saturates separation. A blend of 75 wt % 100N distillate/25 wt % retentate from the membrane extraction run was then prepared and submitted for solvent extraction with N-methyl pyrrolidone (NMP). NMP solvent extraction runs were also made on the MCT-5 distillate feed neat to determine the base case raffinate yield.

As can be seen from Table 1, in this study, Celgard 2500 which is a polypropylene membrane with 0.04×0.20 micrometer pores was used in the membrane separation step, although other micro-porous membranes such as nylon 6,6 or teflon could also have been used. The purpose of the micro-porous membrane was to partition the extract feed from the extraction solvent while still maintaining intimate contact between the two phases. The extraction solvent used in the membrane extraction step was acetonitrile although the process can be extended to other solvents. The separation was carried out at 50° C. As shown in Table 1, mass spec. completed on the permeate and retentate confirm that the desired aromatics/saturates separation was successful by membrane extraction.

After the retentate from the membrane separation step had been generated, it was submitted in an admixture with 100N distillate for NMP (with 0.4% water) solvent extraction. Solvent extraction runs were also made on 100N distillate neat at three different severities by varying treat rate and temperature to determine the base case raffinate yield.

As can be seen from Table 2 a raffinate yield of 56.2 LV % was achieved on the 75 wt %/25 wt % blend of 100N distillate and the retentate from membrane extraction. This compares favorably with a raffinate yield of 49.1 LV % on 100N distillate neat, although the quality of the raffinate from the run on 100N distillate neat was somewhat higher (RI of 1.4449 vs 1.4458 @ 75° C.).

Figure 2:
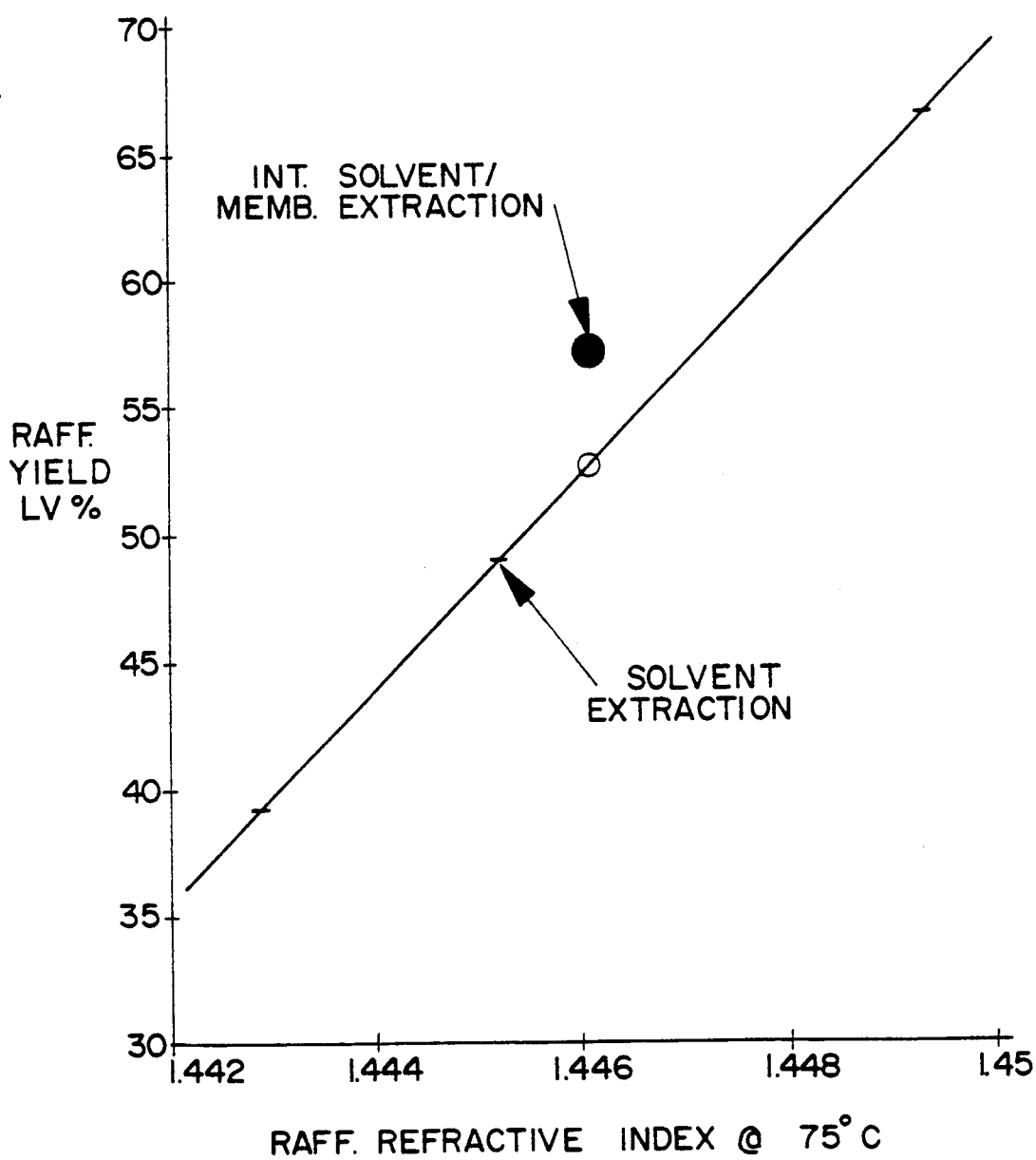
FIG. 2 graphically shows the raffinate yield credit, for practicing the integrated retentate recycle process of the present invention, as a function of constant raffinate quality.

In FIG. 2, the raffinate yield is plotted against the waxy raffinate refractive index. As can be seen from the figure, at a constant raffinate quality, the raffinate yield was higher by about 3 LV % for the 75%/25% blend relative to 100-N neat. This figure further confirms that there are significant credits from the integrated solvent extraction-membrane extraction process as described in this specification.

Although membrane extraction via a microporous membrane was utilized in this patent memorandum, it can be expected that other aromatics/saturates membrane separation processes such as perstraction could also be used to achieve the desired treat of lube extract oil. Also, although data on only a 100 neutral extract oil are shown, it is expected that the benefits of the integration disclosed in this specification to be applicable to other oil grades and other refinery streams where aromatics/saturates separation are needed.

TABLE 1

| MEMBRANE EXTRACTION OF LUBE EXTRACT | | | |
|---|---|---|---|
| Stream | Feed (MCT 5 Extract) | Permeate | Retentate |
| Membrane Extraction | | | |
| Membrane | — | Celgard 2500 | — |
| Solvent | — | Acetonitrile | — |
| Temperature, °C. | — | 50 | — |
| Yield, Wt % | 100.0 | 66.1 | 33.9 |
| Composition, LV % | | | |
| Saturates | 44.3 | 34.2 | 77.3 |
| 1 − R Aromatic | 18.6 | 21.8 | 7.8 |
| 2 − R Aromatic | 16.6 | 19.4 | 7.7 |
| 3 + R Aromatic | 20.5 | 24.6 | 7.2 |

TABLE 2

| BENEFITS DEMONSTRATED FOR INTEGRATED SOLVENT/MEMBRANE EXTRACTION | | | | |
|---|---|---|---|---|
| Stream | 75% MCT 5 Dist/ 25% Retentate | 100% MCT 5 Distillate | | |
| Temp, °C. | 60 | 60 | 50 | 60 |
| Treat, LV % | 320 | 320 | 200 | 480 |
| Raffinate | | | | |
| Yield, LV % | 56.2 | 49.1 | 66.8 | 38.8 |
| RI @ 75° C. | 1.4458 | 1.4449 | 1.4491 | 1.4426 |

Solvent: 0.4% water in NMP

What is claimed is:

1. A process for increasing the yield of raffinate produced in the solvent extraction of hydrocarbons, said process including the steps of contacting a hydrocarbon feed with a selective aromatics extraction solvent to produce a saturates rich raffinate phase and an aromatics rich extract solution phase in a solvent extraction zone, removing the extraction solvent from the extract solution phase to produce recovered solvent and an extract oil, passing the extract oil to a membrane separation process wherein a saturates/1-ring aromatics rich retentate is produced and a 2+ ring aromatics rich permeate is produced and recycling the saturates/1-ring aromatics retentate back to the solvent extraction step for addition to the hydrocarbon feed for processing in the selective solvent extraction step thereby recovering the saturates/1-ring aromatics present in the retentate phase as part of the raffinate from the solvent extraction zone.

2. The process of claim 1 wherein the membrane separation process comprises passing the extract oil along one face of a non-selective porous partition barrier membrane while simultaneously contacting the opposite face of said membrane with an aromatics selective extraction solvent wherein the multi-ring aromatics selectively permeate through the porous partition membrane in response to the selective aromatics extraction solvent yielding a saturates/1-ring aromatics rich retentate and a 2+ ring aromatics rich permeate.

3. The process of claim 2 wherein the selective aromatics extraction solvent used in the membrane separation process is selected from phenol, furfural, sulfolane, N-methyl 2-pyrrolidone and aliphatic polyamines.

4. The process of claim 2 wherein the porous partition barrier has a pore size in the range 100 to 5000 Å.

5. The process of claim 4 wherein the porous partition barrier is an ultrafiltration membrane selected from polyethylene, polypropylene, teflon and cellulose.

6. The process of claim 1 wherein the selective aromatics extraction solvent is recovered from the extract solution phase coming from the solvent extraction process step by distillation.

7. The process of claim 1 wherein the retentate is recycled to the solvent extraction zone in an amount ranging from 5 to 50 wt. % based on feed.

8. The process of claim 1 wherein the hydrocarbon feed boils in the about 320° to 1100° F. range.

* * * * *